US00PP20514P2

(12) United States Plant Patent
Skotak et al.

(10) Patent No.: US PP20,514 P2
(45) Date of Patent: Dec. 1, 2009

(54) ***GUZMANIA* PLANT NAMED 'SKOHICLI'**

(50) Latin Name: ***Guzmania lingulata*×*wittmackii*×*(Guzmania lingulata)***
Varietal Denomination: Skohicli

(76) Inventors: Chester Skotak, Apdo. 652, Alajuela (CR) 4050; Herb Hill, 1040 Jameson Rd., Lithia, FL (US) 33547

( * ) Notice: Subject to any disclaimer, the term of this patent is extended or adjusted under 35 U.S.C. 154(b) by 0 days.

(21) Appl. No.: 12/157,173

(22) Filed: Jun. 6, 2008

(51) Int. Cl.
*A01H 5/00* (2006.01)

(52) U.S. Cl. ..... Plt./371

(58) Field of Classification Search ..... Plt./371
See application file for complete search history.

*Primary Examiner*—Annette H Para

(57) ABSTRACT

A new and distinct *Guzmania* cultivar named 'Skohicli' is disclosed, characterized a compact plant habit, and very large, decorative red bracts.

1 Drawing Sheet

Figure 1:
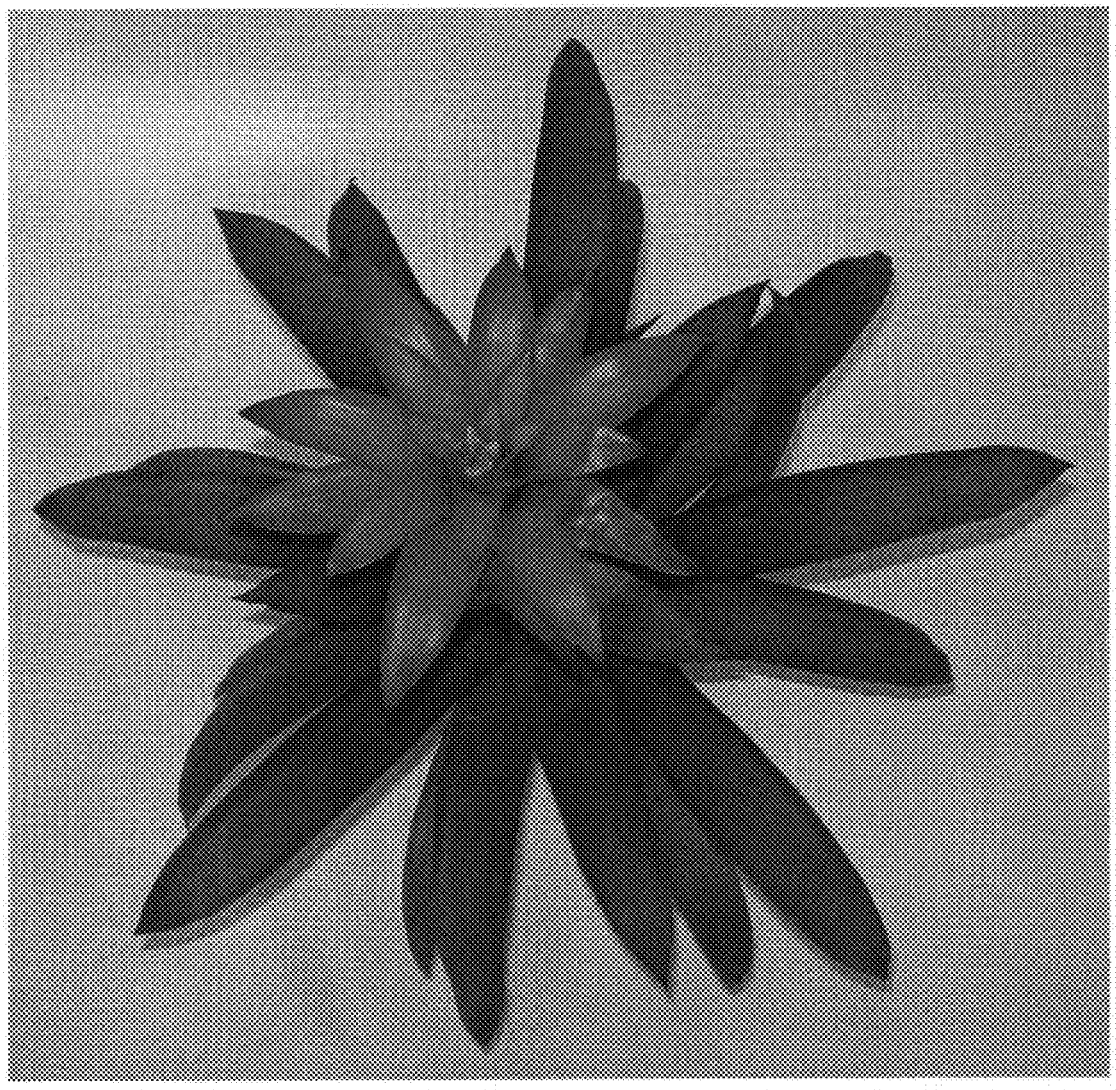

Latin name of the genus and species: *Guzmania lingulata*×*wittmackii*×(*Guzmania lingulata*).

Variety denomination: 'Skohicli'.

BACKGROUND OF THE INVENTION

The new cultivar is a product of a planned breeding program. The new variety originated from a cross pollination of the seed parent, *Guzmania lingulata*×*wittmackii* with the pollen parent *Guzmania lingulata,* directed by the inventors during 1999.

It was discovered by the co-inventors, Chester Skotak Jr., a citizen of Costa Rica, and Herb Hill, a citizen of the United States in 2002 in Ajauela, Costa Rica in a group of seedlings resulting from the 1999 crossing.

Asexual reproduction of the new cultivar 'Skohicli' was first performed in Costa Rica by tissue culture in April 2003. 'Skohicli' has since produced several generations by micropropagation and has shown that the unique features of this cultivar are stable and reproduced true to type.

SUMMARY OF THE INVENTION

The cultivar 'Skohicli' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Skohicli' These characteristics in combination distinguish 'Skohicli' as a new and distinct *Guzmania* cultivar:

1. Compact plant shape.
2. Very large inflorescence.
3. Strong red florescence color.
4. Suitability as an indoor pot plant.

Plants of the new cultivar 'Skohicli' are similar to both parent varieties in most horticultural characterisitics. However, 'Skohicli' differs from both the seed and pollen parents in having a more compact plant shape and larger inflorescence.

COMMERCIAL COMPARISON

'Skohicli' can be compared to the unpatented commercial variety *Guzmania* 'Catherine.' Plants of 'Catherine' are similar to plants of 'Skohicli' in most horticultural charactertistics, however, 'Skohicli' has a wider inflorescence, more compact plant size and shorter, wider leaves than 'Catherine.'

BRIEF DESCRIPTION OF THE PHOTOGRAPH

The accompanying photograph in FIG. 1 illustrates in full color a typical plant of 'Skohicli' grown in a greenhouse. This plant is approximately 2 years old, shown in an 11 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Skohicli' plants grown in a climate controlled greenhouse in Evergem, the Netherlands. Temperatures ranged from 20° C. to 28° C. night and day. No artificial light, photoperiodic treatments or chemical treatments were given to the plants. Measurements and numerical values represent averages of typical plant types.

Botanical classification: *Guzmania* hybrid. cultivar 'Skohicli.'

PLANT

Growth habit: Upright, flattened sphere, forming compact rosettes around a single axis. One straight, upright inflorescence arising from the center of plant.

Height: Approximately 34.3 cm.

Plant spread: Approximately 48.8 cm in a 11 cm pot.

Normal pot size: 9, 11 cm.
Growth rate: Slow.
Branching characteristics: Upright, non-branching.
Number of leaves per stem: Approximately 26.
Age of plant described: Approximately 2 years.

FOLIAGE

Leaf:

*Arrangement.*—Whorled, single occurring basal rosettes.
*Average length.*—Approximately 26.8 cm.
*Average width.*—Approximately 4.0 cm.
*Shape of blade.*—Ligulate.
*Aspect.*—Slightly recurved.
*Apex.*—Apiculate.
*Base.*—Sheathing.
*Margin.*—Entire.
*Texture of top surface.*—Smooth, moderately glossy.
*Texture of bottom surface.*—Smooth, moderately glossy.
*Color.*—Young foliage upper side: Green to yellow-green; in between RHS 137B and 146A, middle part striped with both RHS greyed-orange, 177A and 77B base lighter yellow green; between RHS 146C and 146D. Young foliage under side: Yellow-green; near RHS 146A flushed RHS greyed-purple; 187A, middle sections RHS greyed-purple; 187A, lighter towards the base; 187B. Mature foliage upper side: Green to yellow-green; in between RHS 143A and 146A, base light yellow-green; RHS 146D Mature foliage under side: Yellow-green; RHS 146A, slightly flushed greyed-purple towards the base; between RHS 187A and 187B.
*Venation.*—Type: Parallel. Venation coloration: Identical/Indistinguishable from foliage.

Petiole: Not present, sessile.

INFLORESCENCE

General description: Simple spike (scape) consisting of many bracts only. No individual flowers are visible. Spike emerges from the centre of the rosette. Inflorescence is formed by conspicuous bracts.

*Inflorescence height.*—29.5 cm.
*Inflorescence width.*—19.3 cm.

Peduncle

*Length.*—22.0 cm.
*Width.*—1.1 cm.
*Aspect.*—Very straight, 90° angle to rosette.
*Strength.*—Very strong.
*Color.*—Near RHS. White 157 A.

Bracts

*Shape.*—Ligulate.
*Length.*—12.1 cm.
*Width.*—3.5 cm.
*Tip.*—Acute.
*Base.*—Sheathed.
*Margin.*—Entire.
*Color upperside.*—Near RHS Red 42A.
*Color underside.*—Between RHS Red 40A and Red 42A.
*Coloration scape bracts.*—Upperside: Near RHS Orange-Red 35A Upperside Top: Near RHS Green 137A. Upperside Outermost Tip: Near RHS Greyed-Purple 187A. Underside: Near RHS Orange-Red 34A Underside Top: Near RHS Red 53A with flush of Yellow-Green 147A. Underside Outermost Tip: Near RHS Greyed-Purple 187B.

OTHER CHARACTERISTICS

Disease resistance: Neither resistance nor susceptibility to diseases or pests has been observed in this variety.
Drought tolerance and cold tolerance: Observed to tolerate temperatures to 40° C. without any negative effects. Temperature tolerance above this range has not been observed. Tolerance of cold temperatures has not been observed.
Fruit/seed production: Not observed.

What is claimed is:

1. A new and distinct cultivar of *Guzmania* plant named 'Skohicli' as herein illustrated and described.

* * * * *